United States Patent
Nadzadi et al.

(10) Patent No.: US 9,724,109 B2
(45) Date of Patent: Aug. 8, 2017

(54) SYSTEMS AND METHODS FOR PREPARING A PROXIMAL TIBIA

(71) Applicant: MAKO Surgical Corp., Fort Lauderdale, FL (US)

(72) Inventors: Mark Nadzadi, Memphis, TN (US); Ali Abbasi, Davie, FL (US); Amit Mistry, Fort Lauderdale, FL (US); Jason Otto, Plantation, FL (US)

(73) Assignee: MAKO Surgical Corp., Fort Lauderdale, FL (US)

( * ) Notice: Subject to any disclaimer, the term of this patent is extended or adjusted under 35 U.S.C. 154(b) by 126 days.

(21) Appl. No.: 14/579,730

(22) Filed: Dec. 22, 2014

(65) Prior Publication Data

US 2015/0182237 A1    Jul. 2, 2015

Related U.S. Application Data

(60) Provisional application No. 61/922,723, filed on Dec. 31, 2013.

(51) Int. Cl.
*A61B 17/16* (2006.01)
*A61B 17/17* (2006.01)
(Continued)

(52) U.S. Cl.
CPC ...... *A61B 17/1764* (2013.01); *A61B 17/1675* (2013.01); *A61B 34/30* (2016.02); *A61F 2/461* (2013.01)

(58) Field of Classification Search
CPC .......................... A61B 17/1675; A61F 2/389
See application file for complete search history.

(56) References Cited

U.S. PATENT DOCUMENTS

D622,854 S    8/2010    Otto et al.
D625,415 S   10/2010    Otto et al.
(Continued)

FOREIGN PATENT DOCUMENTS

WO   WO-2012/158604   11/2012
WO   WO-2013/101753    7/2013

OTHER PUBLICATIONS

U.S. Appl. No. 14/578,007, filed Dec. 19, 2014, Mako Surgical Corp.
(Continued)

*Primary Examiner* — David Bates
*Assistant Examiner* — Olivia C Chang
(74) *Attorney, Agent, or Firm* — Foley & Lardner LLP (57) ABSTRACT

A method of preparing a tibia to receive a tibial implant component includes performing a first set of cuts to prepare a floor interface surface on the tibia, wherein the floor interface surface includes a portion on each side of a tibial eminence extending above the floor interface surface on the tibia. The method further includes performing a second set of cuts to prepare a tibial eminence wall interface surface, wherein the wall interface surface extends substantially perpendicular to the floor interface surface between the floor interface surface and a top surface of the tibial eminence. The method further includes performing a third set of cuts to prepare a radiused intersection between the floor interface surface and the wall interface surface. The sets of cuts are performed subject to a cutting restraint guide. At least one set of cuts may be performed using a rotary cutter.

7 Claims, 9 Drawing Sheets

(51) Int. Cl.
*A61F 2/46* (2006.01)
*A61B 34/30* (2016.01)

(56) References Cited

U.S. PATENT DOCUMENTS

| | | | |
|---|---|---|---|
| D626,234 S | 10/2010 | Otto et al. | |
| 7,842,092 B2 | 11/2010 | Otto et al. | |
| 8,010,180 B2 | 8/2011 | Quaid et al. | |
| 8,475,535 B2 | 7/2013 | Otto | |
| 8,702,803 B2 | 4/2014 | Otto et al. | |
| 8,911,501 B2 | 12/2014 | Irwin et al. | |
| 8,977,021 B2 | 3/2015 | Kang et al. | |
| 2007/0270685 A1* | 11/2007 | Kang | A61B 19/5244 600/424 |
| 2008/0058945 A1 | 3/2008 | Hajaj et al. | |
| 2008/0262812 A1 | 10/2008 | Arata et al. | |
| 2010/0094429 A1 | 4/2010 | Otto | |
| 2010/0153076 A1 | 6/2010 | Bellettre et al. | |
| 2010/0153081 A1 | 6/2010 | Bellettre et al. | |
| 2010/0170362 A1 | 7/2010 | Bennett et al. | |
| 2010/0217400 A1 | 8/2010 | Nortman et al. | |
| 2011/0066079 A1 | 3/2011 | Otto et al. | |
| 2011/0264097 A1* | 10/2011 | Hodorek | A61F 2/389 606/88 |
| 2012/0310617 A1 | 12/2012 | Bellettre et al. | |
| 2013/0172783 A1 | 7/2013 | Ikits et al. | |
| 2013/0173008 A1 | 7/2013 | Bechtold et al. | |
| 2014/0180290 A1 | 6/2014 | Otto et al. | |
| 2014/0188134 A1 | 7/2014 | Nortman et al. | |
| 2014/0189508 A1 | 7/2014 | Granchi et al. | |

OTHER PUBLICATIONS

U.S. Appl. No. 14/578,064, filed Dec. 19, 2014, Mako Surgical Corp.
U.S. Appl. No. 14/640,895, filed Mar. 6, 2015, Mako Surgical Corp.
U.S. Appl. No. 14/640,919, filed Mar. 6, 2015, Mako Surgical Corp.
U.S. Appl. No. 29/329,712, filed Dec. 19, 2008, Otto.
U.S. Appl. No. 29/329,715, filed Dec. 19, 2008, Otto.
U.S. Appl. No. 29/466,144, filed Sep. 4, 2013, Mako Surgical Corp.
U.S. Appl. No. 29/466,147, filed Sep. 4, 2013, Mako Surgical Corp.
U.S. Appl. No. 29/466,148, filed Sep. 4, 2013, Mako Surgical Corp.
International Search Report and Written Opinion for PCT Application No. PCT/US2014/071961, dated Mar. 25, 2015, 14 pages.

* cited by examiner

SYSTEMS AND METHODS FOR PREPARING A PROXIMAL TIBIA

CROSS-REFERENCE TO RELATED APPLICATIONS

This application claims the benefit of and priority to U.S. Provisional Patent Application Ser. No. 61/922,723, filed Dec. 31, 2013, the disclosure of which is hereby incorporated by reference in its entirety.

BACKGROUND

The present disclosure relates generally to systems and methods for performing resection of bone, and more particularly to systems and methods for preparing the proximal tibia to receive a tibial prosthetic implant component.

The knee joint comprises the interface between the distal end of the femur and the proximal end of the tibia. In a properly-functioning knee joint, medial and lateral condyles of the femur pivot smoothly along menisci attached to respective medial and lateral condyles of the tibia. When the knee joint is damaged, the natural bones and cartilage that form the joint may be unable to properly articulate, which can lead to joint pain and, in some cases, interfere with normal use of the joint In some situations, surgery is required to restore normal use of the joint and reduce pain. Depending upon the severity of the damage, the surgery may involve partially or completely replacing the joint with prosthetic components. During such knee replacement procedures, a surgeon resects damaged portions of the bone and cartilage, while attempting to leave healthy tissue intact. The surgeon then fits the healthy tissue with artificial prosthetic components designed to replicate the resected tissue and restore proper knee joint operation.

One knee replacement procedure—total knee arthroplasty ("TKA")—involves the resection of some or all of each of the medial and lateral condyles of both the femur and tibia and the removal of the fibro-cartilage menisci located at the femorotibial interface. A prosthetic femoral component, typically made of cobalt-chromium alloy or other strong, surgical-grade metal, is fitted and secured to the distal end of the femur to replace the resected portion of the femur. Similarly, a prosthetic tibial component, the base of which is also typically made of cobalt-chromium alloy, titanium, or other suitable metal, is fitted and secured to the proximal end of the tibia to replace the resected portion of the tibia.

In some situations, the patient's bone at the knee joint may have deteriorated to a point which requires TKA surgery, but one or more of the patient's cruciate ligaments (e.g., the anterior cruciate ligament (ACL) and/or posterior cruciate ligament (PCL)) are in sufficient condition to provide adequate joint stability. Maintaining the native cruciate ligaments is often advantageous, as doing so is generally thought to aid in proprioception (the ability to sense where parts of the body are in relation to each other) and could make activities like climbing stairs feel more stable or natural. Preserving the cruciate ligaments can also promote more normal front to back knee motion, which can enhance the patient's ability to maintain preoperative range of motion, particularly as it relates to deep flexion. The ligaments also aid in joint stability.

Each of the native cruciate ligaments connects to one of the femoral condyles, passes within the intercondylar region of the femur, and connects to the center-top portion of the tibia called the tibial eminence. In order to accommodate the passage of the cruciate ligaments, the femoral and tibial implant components used in cruciate-retaining procedures typically comprise intercondylar cutaways that define a vertical passage between the intercondylar fossa of the femur and the tibial eminence. The medial and lateral components of each of the femoral and tibial prosthetic components are separated by a deep intercondylar passage (or "notch") that allows for passage of cruciate ligaments vertically through the notch.

During normal operation of the knee joint, the cruciate ligaments can exert significant tension at the attachment site of the tibia called the tibial eminence. In a healthy knee joint, there is sufficient tissue surrounding the tibial eminence to aid in the distribution of this force across the surface of the tibia. Installation of a cruciate-retaining tibial prosthetic component, while aimed at preserving an attachment site at the tibial eminence, typically requires significant removal of the surrounding native tissue of the tibia to make way for installation of the tibial implant. This surrounding tissue provides much of the attachment strength that counteracts the tension applied by the cruciate ligaments, and removal of this tissue can weaken the attachment strength of the tibial eminence.

Present methods of tibial preparation (i.e. removal of bone to receive the tibial implant) can result in inadvertent removal of even more tissue than is necessary for installation of the tibial implant, which further weakens the strength of the tibial eminence and can result in implant failure. In particular, present methods employ manual oscillating sagittal saws to make planar cuts. Manual saws making horizontal cuts can overcut into the eminence, and manual saws making vertical cuts can cut too deep into the tibial bone. These overcuts weaken the tibial eminence and the cruciate ligament attachment. Additionally, traditional planar saws can create sharp corners and high stress risers, which puts additional stress at the tibial eminence. Attempts to improve the undercut problem, particularly at the lateral overcuts, and reduce stress risers, have led to adding drilled pins placed at the intersection of the resected portion and the remaining tibial eminence portion to stop overcutting. However, saw blades often skive and can still result in overcutting and stress risers.

SUMMARY

One embodiment of the invention relates to a method of preparing a tibia to receive a tibial implant component. The method includes performing a first set of cuts to prepare a floor interface surface on the tibia, wherein the floor interface surface includes a portion on each side of a tibial eminence extending above the floor interface surface on the tibia. The method further includes performing a second set of cuts to prepare a tibial eminence wall interface surface, wherein the wall interface surface extends substantially perpendicular to the floor interface surface between the floor interface surface and a top surface of the tibial eminence. The method further includes performing a third set of cuts to prepare a radiused intersection between the floor interface surface and the wall interface surface. The sets of cuts are performed subject to a cutting restraint guide.

According to another embodiment, a surgical planning method for preparing a tibia to receive a tibial implant component includes acquiring a representation of a proximal end of the tibia and acquiring a representation of a tibial implant. The planning method further includes positioning the representation of the tibial implant on the representation of the proximal end of the tibia and planning preparation of the proximal end of the tibia based on the tibial implant. The planning preparation of the proximal end of the tibia includes planning a first set of cuts to prepare a floor interface surface on the tibia, wherein the floor interface surface comprises a portion on each side of a tibial eminence extending above the floor interface portion on the tibia; planning a second set of cuts to prepare a tibial eminence wall interface surface, wherein the wall interface surface extends substantially perpendicular to the floor interface between the floor interface surface and a top surface of the tibial eminence; and planning a third set of cuts to prepare a radiused intersection between the floor interface surface and the wall interface surface. The method further includes providing a cutting restraint guide based on the plan of at least one of the first, second, and third sets of cuts.

According to another embodiment, a surgical system includes a surgical device configured to hold a surgical tool and be manipulated by a user to perform preparation of a tibia to receive an implant component, and a cutting restraint guide configured to provide a constraint on movement of the surgical tool. The cutting restraint guide is configured to allow a user to perform a plurality of cuts including a first set of cuts to prepare a floor interface surface on the tibia, wherein the floor interface surface comprises a portion on each side of a tibial eminence extending above the floor interface portion on the tibia; a second set of cuts to prepare a tibial eminence wall interface surface, wherein the wall interface surface extends substantially perpendicular to the floor interface between the floor interface surface and a top surface of the tibial eminence; and a third set of cuts to prepare a radiused intersection between the floor interface surface and the wall interface surface.

It is to be understood that both the foregoing general description and the following detailed description are exemplary and explanatory only and are not restrictive of the invention, as claimed.

BRIEF DESCRIPTION OF THE FIGURES

The accompanying drawings, which are incorporated in and constitute a part of this specification, illustrate several embodiments that, together with the description, serve to explain the principles and features of the present disclosure.

DETAILED DESCRIPTION

Reference will now be made in detail to exemplary embodiments of the present disclosure, examples of which are illustrated in the accompanying drawings.

A healthy knee joint comprises the interface between the distal end of the femur and the proximal end of the tibia. If the healthy knee joint becomes damaged due, for example, to injury or disease, knee surgery may be required to restore normal structure and function of the joint. If the damage to the knee is severe, total knee arthroplasty ("TKA") may be required. TKA typically involves the removal of the damaged portion of joint and the replacement of the damaged portion of the joint with one or more prosthetic components.

In some TKA procedures, one or more of cruciate ligaments (including anterior cruciate ligament and/or posterior cruciate ligament) may be left intact, to be re-used with the prosthetic implants to form the new knee joint. In these "cruciate-retaining" applications, the prosthetic implant components may be configured to avoid interference with or impingement on the retained cruciate ligaments passing through the intercondylar area of the knee joint. For example, each of the femoral and tibial prosthetic components may be designed with a intercondylar "notch" that extends from the posterior of the prosthetic component toward the anterior of the prosthetic component. The femoral and tibial intercondylar notches overlap in the vertical direction, providing a passage that allows the cruciate ligament to pass from the femoral intercondylar fossa down to the tibial eminence.

Because cruciate ligaments are exposed to significant tensile force during normal knee joint use, it is important that the attachment sites where the cruciate ligaments attach to the femur and tibia have sufficient strength to properly anchor the cruciate ligaments to the bone. Otherwise, the force applied by the cruciate ligament strains the tissue around the attachment site, possibly leading to failure of the joint, which may require corrective surgery to repair. One way to limit the possibility of such a failure is to limit and carefully control the amount of bone resected at or near the attachment site(s) (i.e., the intercondylar fossa of the femur and tibial eminence 101a of the tibia). Limiting the amount of disturbance of native tissue at the attachment sites helps preserve the natural anchoring mechanism of the tissue, which decreases the likelihood of failure at the attachment site.

Figure 1:
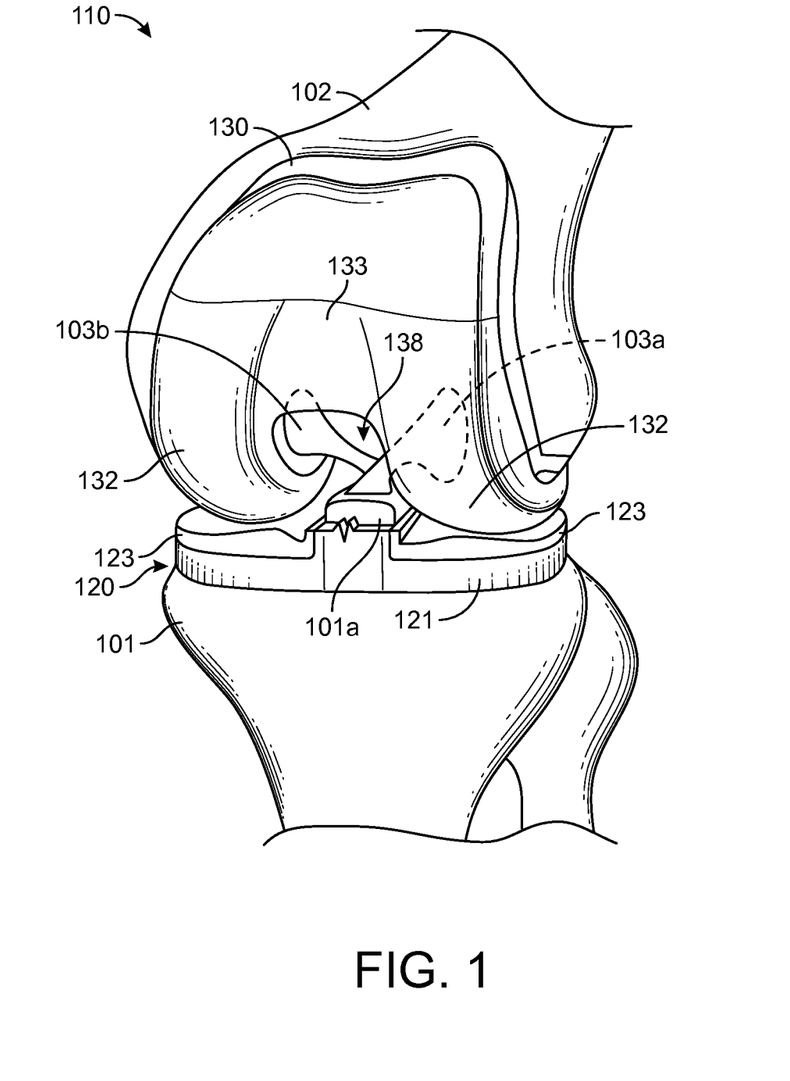
FIG. 1 illustrates a perspective view of a post-operative prosthetic knee joint fitted with a prosthetic system, consistent with an exemplary embodiment.

In the embodiment illustrated in FIG. 1, prosthetic implant system 110 includes a number of components configured to replace a resected portion of a native knee joint. According to one embodiment, prosthetic implant system 110 includes a tibial implant system 120 configured to replace a resected portion of a native tibia 101. Prosthetic implant system 110 also includes a femoral component 130 configured to replace a resected portion of a native femur 102. After implantation during knee replacement surgery, tibial implant system 120 and femoral component 130 cooperate to replicate the form and function of the native knee joint.

Femoral component 130 is secured to the distal end of femur 102 and configured to replace the structure and function of the native femoral portion of knee joint 100. As such, femoral component 130 may be manufactured from surgical-grade metal or metal alloy material (such as surgical-grade steel, titanium or titanium allow, a cobalt-chromium alloy, a zirconium alloy, or tantalum) that is substantially rigid for providing sufficient strength to support the forces required of the knee joint. According to one embodiment, femoral component 130 may embody a single component having a plurality of different structural features, each configured to perform a particular function associated with the knee joint 100. For example, femoral component 130 may include a pair of condyles 132, each of which is coupled to a patellar guide portion 133. The pair of condyles 132 are separated from one another by an intercondylar notch 138, which provides a channel through which one or more cruciate ligaments 103, such as anterior cruciate ligament (ACL) 103a and/or posterior cruciate ligament (PCL) 103b, may pass.

Tibial implant system 120 may include a plurality of components that cooperate to provide a stable surface that articulates with femoral component 130 to restore proper knee joint function. As illustrated in FIG. 1, tibial implant system 120 includes a base portion 121 and one or more insert portions 123. During a knee replacement procedure, base portion 121 is secured to the proximal end of the tibia 101, which has been surgically prepared by removing damaged bone and tissue and reshaping the healthy bone to receive the base portion 121. Once base portion 121 is secured to tibia 101, the surgeon completes assembly of tibial implant system 120 by engaging and securing insert portions 123 within base portion 121. Base portion 121 of tibial prosthetic system may be configured with a passage through the center to allow for connection between the retained cruciate ligaments 103 and tibial eminence 101a.

Base portion 121 may be configured to emulate the structure and function of the top surface of tibia 101. Thus, similar to femoral component 130, base portion 121 may be manufactured from surgical-grade metal or metal alloy material (such as surgical-grade steel, titanium or titanium allow, a cobalt-chromium alloy, a zirconium alloy, or tantalum) that is substantially rigid for providing a stable base upon which to reconstruct the remainder of the prosthetic joint.

Insert portions 123 may be designed to emulate the form and function of certain components of the natural femorotibial interface, including, among other things, medial and lateral menisci of the knee joint. As such, insert portions 123 may be constructed of smooth, semi-rigid synthetic or semi-synthetic plastic, rubber, or polymer material. Insert portions 123 may be configured to provide a smooth surface that is designed to articulate with a femoral component 130 during normal knee operation. According to one embodiment, insert portions 123 are configured to removably engage with base portion 121. Accordingly, insert portions 123 are configured for periodic replacement if insert portions 123 deteriorate over time due, for example, to excessive wear.

Figure 2:
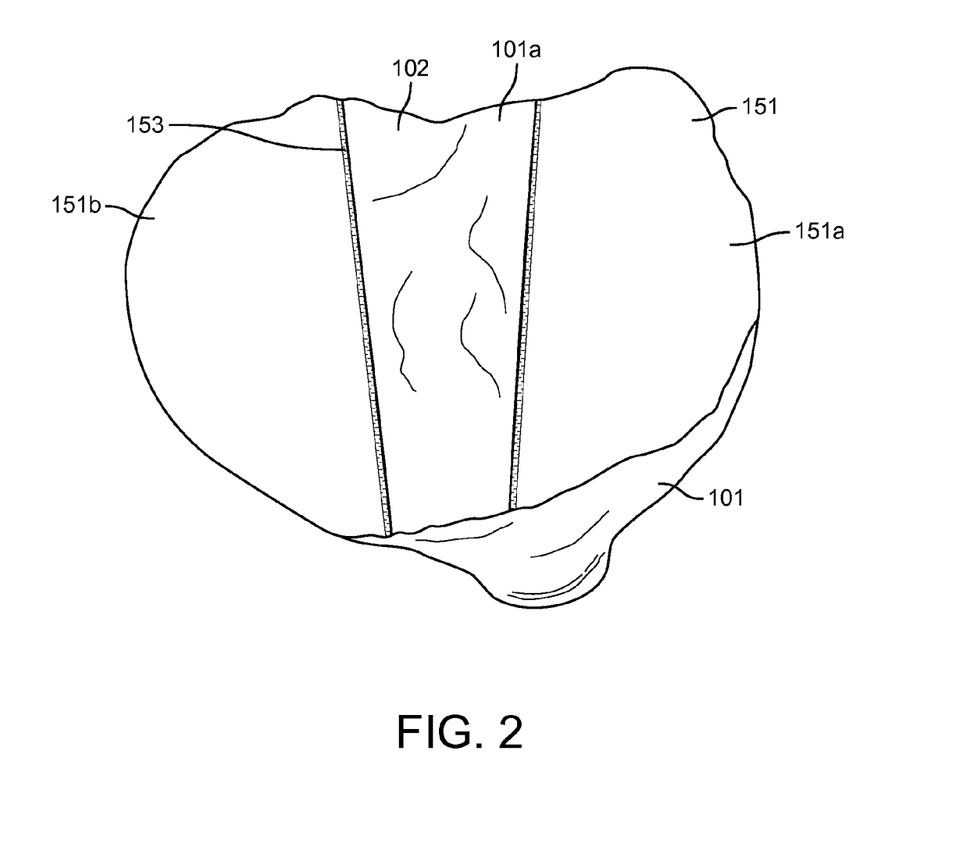
FIG. 2 illustrates a top view of a proximal end of a tibia prepared to receive a prosthetic component according to a traditional method.

FIG. 2 depicts the proximal end of the tibia 101 prepared to receive a tibial implant system, such as base portion 121 of tibial implant system 120, prepared according to a traditional method. As shown, the prepared tibia 101 has a floor interface surface 151, having floor interface surface portions 151a, 151b on each side of tibial eminence 101a. The tibia 101 also has a wall interface surface 153 extending substantially perpendicular to floor interface surface 151 between the floor interface surface 151 and a top surface 102 of the tibial eminence 101a. Preparation of the tibia as shown in FIG. 2, according to a traditional method, uses a traditional saw, such as an oscillating sagittal saw or reciprocal saw, to make both the horizontal (to form the floor interface surface) and the vertical (to form the wall interface surface) cuts.

Performing these two sets of cuts, in order to maintain a tibial eminence portion 101a in the prepared bone, requires very controlled delineation. Often, these cuts result in overcutting in either the horizontal or vertical direction, and therefore compromising the strength of the tibial eminence 101a. In some practices of this traditional method, drilled pins may be added at the intersection between the floor interface surface 151 and the tibial eminence 101a to stop overcutting and to help reduce stress risers. Nevertheless, saw blades tend to skive and can still overcut while making the horizontal or vertical cuts in the tibia 101. Furthermore, this additional disruption of the bone creates an additional violation of the bone.

Furthermore, as shown in FIG. 2, the use of the sagittal saw creates sharp corners. For example, the intersection between the floor interface portion 151 and the wall interface portion 153, as well as the intersection between the wall interface portion 153 and the top surface 102 of the tibial interface 101a, form sharp edges which can lessen cause stresses to the tibial eminence and reduce its overall strength.

Figure 3:
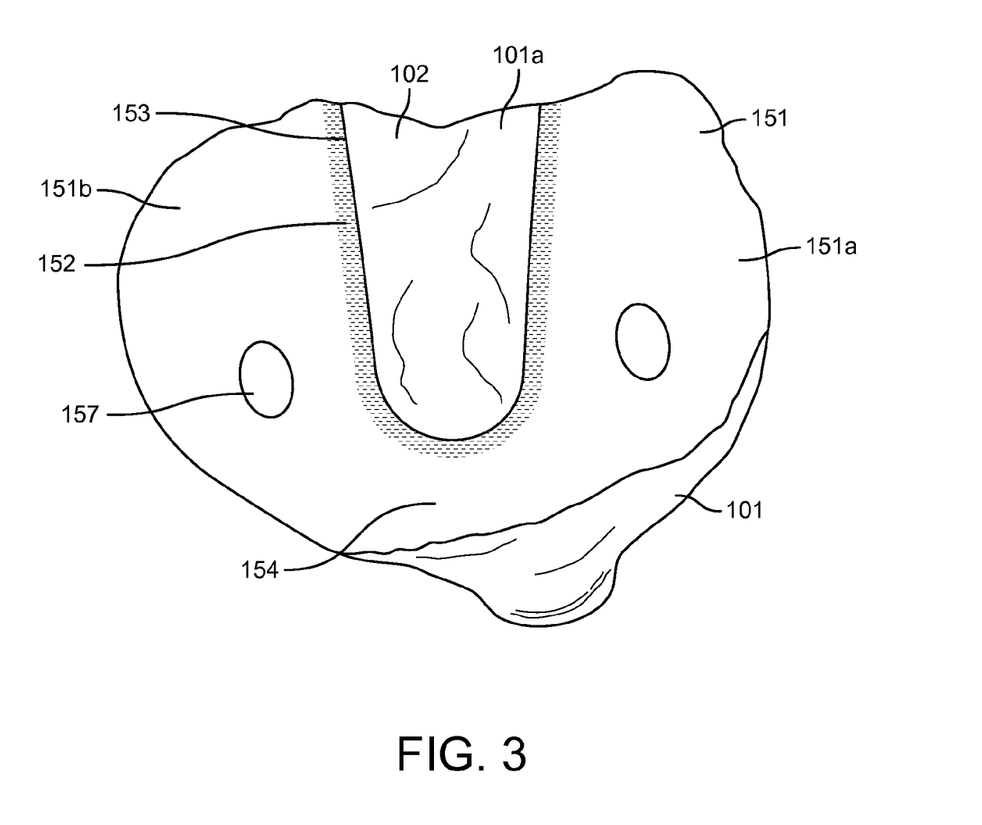
FIG. 3 illustrates a top view of a proximal end of a tibia prepared to receive a prosthetic component according to an exemplary embodiment.
Figure 4:
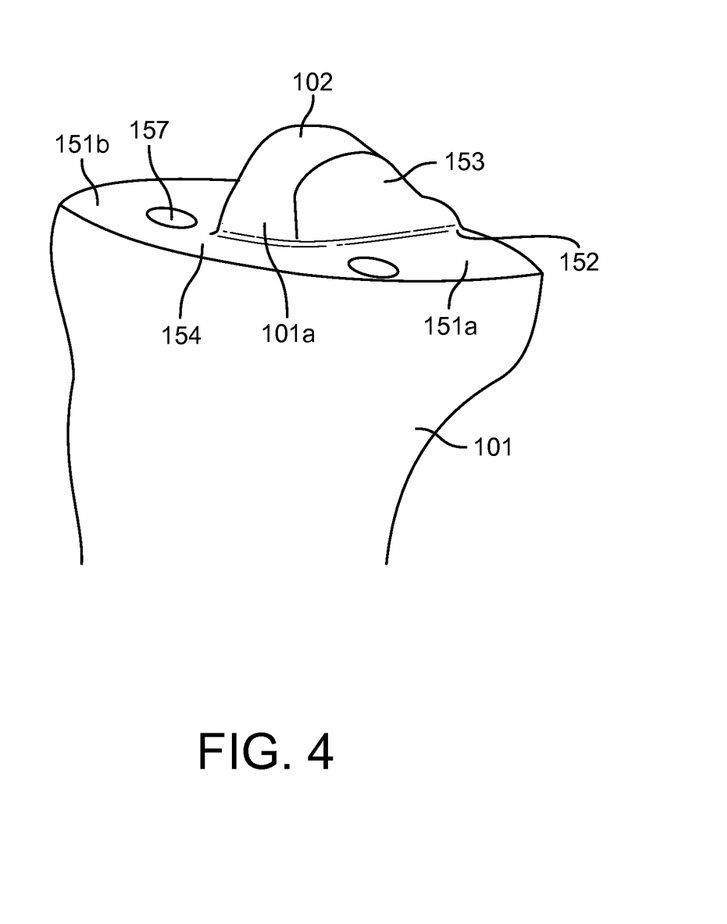
FIG. 4 illustrates a perspective view of a proximal end of a tibia prepared to receive a prosthetic component according to an exemplary embodiment.

FIGS. 3 and 4 depict the proximal end of the tibia 101 prepared to receive a tibial implant system, such as base portion 121 of tibial implant system 120, prepared according to the exemplary embodiments disclosed herein. As shown, the prepared tibia 101 has a floor interface surface 151, having floor interface surface portions 151a, 151b on each side of tibial eminence 101a. The tibia 101 also has a wall interface surface 153 extending substantially perpendicular to floor interface surface 151 between the floor interface surface 151 and a top surface 102 of the tibial eminence 101a. The tibia 101 also has a bridge portion 154 between the floor interface surface portions 151a, 151b at an anterior end of the tibial eminence 101a. Finally, tibia 101 has a curved or radiused intersection 152 between the floor interface surface 151 and the wall interface surface 153.

Preparation of the tibia as shown in FIGS. 3 and 4 may be performed using a number of different surgical cutting tools. As with the traditional method, in a first set of cuts, the floor interface surface 151 may be prepared using an oscillating surgical saw. In a second set of cuts, the wall interface surface 153 may also be prepared using a sagittal saw or a reciprocal saw. As shown in FIGS. 3 and 4, according to an exemplary embodiment, a third set of cuts (which may be prepared in combination with the first or second set of cuts for preparing the floor interface 151 surface or the wall interface surface 153, respectively) is prepared to form a radiused intersection 152 between the floor interface surface 151 and the wall interface surface 153. The radiused intersection 152 is preferably formed using a rotary cutting tool such as a burr or rasp. The intersection 152 may be performed by a rotary cutter having a large radius, wherein a single pass is needed to create the radiused intersection, or a tool having a smaller geometry may be used to perform a sculpture milling technique to form the radiused intersection. In a preferred embodiment, the wall interface surface 153 is also prepared using a rotary cutter such as a burr or cylindrical rasp. In this way, both the intersection 152 and the top corners between the wall interface surface 153 and the top surface 102 of the tibial eminence 101a are rounded. Also, other sharp edges and stress risers can be minimized through the use of the rotary cutter for the wall interface surface 153, to include forming the radiused intersection 152. In other embodiments, preparation of the floor interface surface 151 may also be performed using a rotary cutting tool, such as a burr or cylindrical rasp. As such, any of the first, second, or third sets of cuts may be performed using a rotary cutter, in accordance with the present disclosure. The anterior bridge 154 may be punched or rongeured. In a preferred embodiment, the anterior bridge 154 is also formed using a rotary cutter.

The tibia 101 depicted in FIGS. 3 and 4 also has prepared therein peg apertures 157, which may be drilled or burred using the rotary cutter into the floor interface surface 151. The peg apertures 157 are configured to receive elongated projections from the tibial implant system 120, to further secure the implant to the bone, and resist movement between the implant and the bone. Similarly, the bone may be prepared with keels (not shown) which interface with keels on the tibial implant system 120, and which also improve the security between the bone and the implant.

Figure 5:
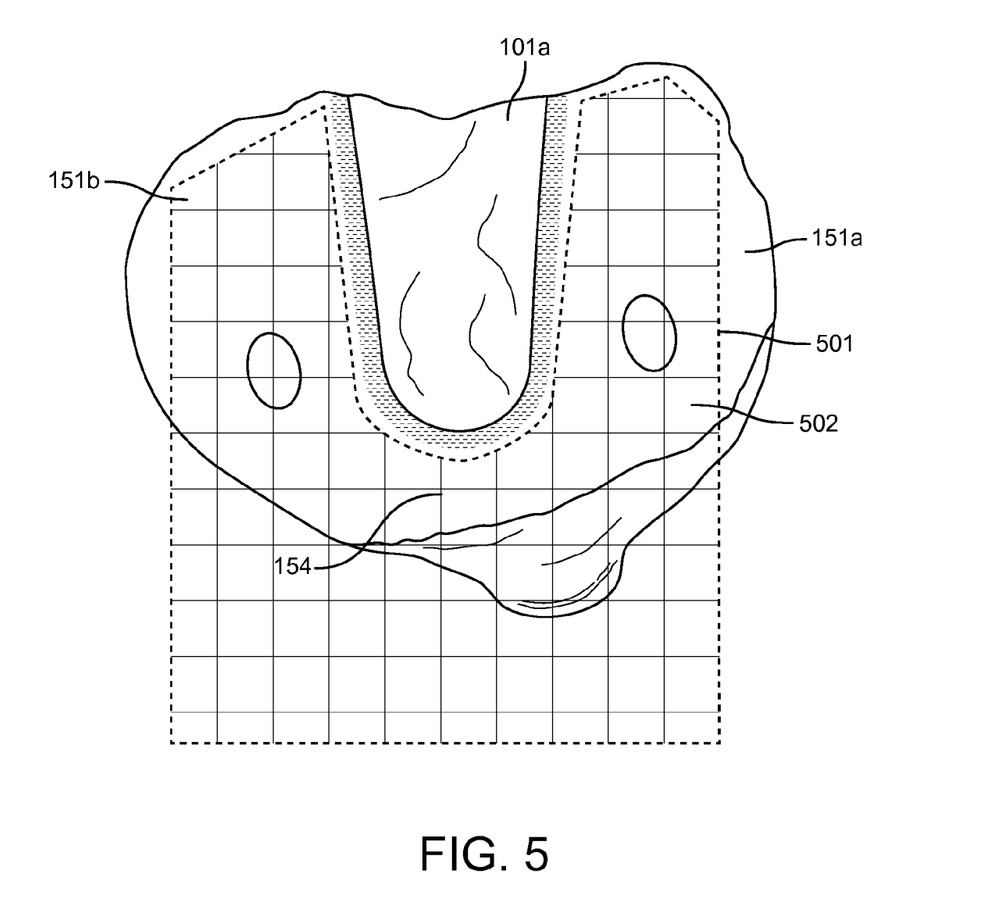
FIG. 5 illustrates a virtual representation of a haptic boundary according to an exemplary embodiment.

Methods of preparing the tibia to receive a tibial implant system also include utilizing precise cutting boundaries so as to limit the amount of overcutting that can compromise the strength of the tibial eminence 101a. FIG. 5 depicts one embodiment of a cutting restraint guide used in the exemplary methods of this disclosure. The figure shows implementation of a haptic boundary 501, provided in conjunction with a surgical system (described in greater detail below), to control the cuts made during preparation of the bone. A surgical system, such as system 200 depicted in FIG. 8, may be configured to establish a virtual haptic geometry associated with the planned prosthetic implant component and associated with or relative to one or more features of a patient's anatomy. The surgical system 200 may be configured to create a virtual representation of a surgical site that includes, for example, virtual representations of a patient's anatomy, a surgical instrument to be used during a surgical procedure, a probe tool for registering other objects within the surgical site, and any other such object associated with a surgical site.

In addition to physical objects, surgical system 200 may be configured to generate virtual objects that exist in software and may be useful during the performance of a surgical procedure. For example, surgical system 200 may be configured to generate virtual boundaries, such as haptic boundary 501, that correspond to a surgeon's plan for preparing a bone, such as boundaries defining areas of the bone that the surgeon plans to cut, remove, or otherwise alter. Alternatively or additionally, surgical system 200 may define virtual objects that correspond to a desired path or course over which a portion of surgical tool 210 should navigate to perform a particular task.

Virtual boundaries and other virtual objects may define a point, line, or surface within a virtual coordinate space (typically defined relative to an anatomy of a patient) that serves as a boundary at which haptic feedback is provided to a surgical instrument when the tracked position of the surgical instrument interacts with the virtual boundary or object. For example, as the surgeon performs a bone cutting operation, a tracking system of the surgical system 200 tracks the location of the cutting tool and, in most cases, allows the surgeon to freely move the tool in the workspace. However, when the tool is in proximity to a virtual haptic boundary (that has been registered to the anatomy of the patient), surgical system 200 controls the force feedback system to provide haptic guidance that tends to constrain the surgeon from penetrating the virtual haptic boundary with the cutting tool. For example, a virtual haptic boundary may be associated with the geometry of a virtual model of a prosthetic implant, and the haptic guidance may comprise a force and/or torque that is mapped to the virtual boundary and experienced by the surgeon as resistance to constrain tool movement from penetrating the virtual boundary. Thus, the surgeon may feel as if the cutting tool has encountered a physical object, such as a wall. Accordingly, the force feedback system of the surgical system 200 communicates information to the surgeon regarding the location of the tool relative to the virtual boundary, and provides physical force feedback to guide the cutting tool during the actual cutting process. In this manner, the virtual boundary functions as a virtual cutting guide. The force feedback system of the surgical system 200 may also be configured to limit the user's ability to manipulate the surgical tool.

As shown in FIG. 5, exemplary haptic boundary 501 is generated to allow manipulation of a surgical tool in the working area 502. The haptic boundary 501 is positioned around the desired tibial eminence area 101a. In this way, the surgeon is able to make cuts to the tibia 101 to create the floor interface surface 151 and anterior bridge portion 154, without overcutting to compromise the strength of the tibial eminence 101a. As shown, haptic boundary 501 is created at a desired offset from the planned tibial eminence 101a so as to keep the tool from cutting too closely. The haptic boundary 501 may be automatically generated based on the tibial implant system to be used and may also be customized by the surgeon. For example, the surgeon may want to increase or decrease the size of the haptic boundary 501, may want to change the boundary offset from the planned tibial eminence 101a, or may want to reposition the planned implant system on the patient's anatomy, and therefore reposition the haptic boundary 501. The surgical system 200 may be configured to allow these inputs by the surgeon through a user interface. Additional haptic boundaries may be generated and applied to the surgical tool for the other sets of cuts, such as for cutting the wall interface surface, to complete the bone preparation according to the disclosed embodiments.

The use of the haptic boundaries generated and applied through a surgical system is one mechanism for creating a cutting restraint guide for performing the present methods. Other embodiments of the cutting restraint guide include a mechanical restraint that may be applied to the cutting tool or to an arm holding the cutting tool, or may be cutting blocks that are created specific to the surgical plan to allow a surgeon to manipulate the tools according to the surgical plan.

Figure 6:
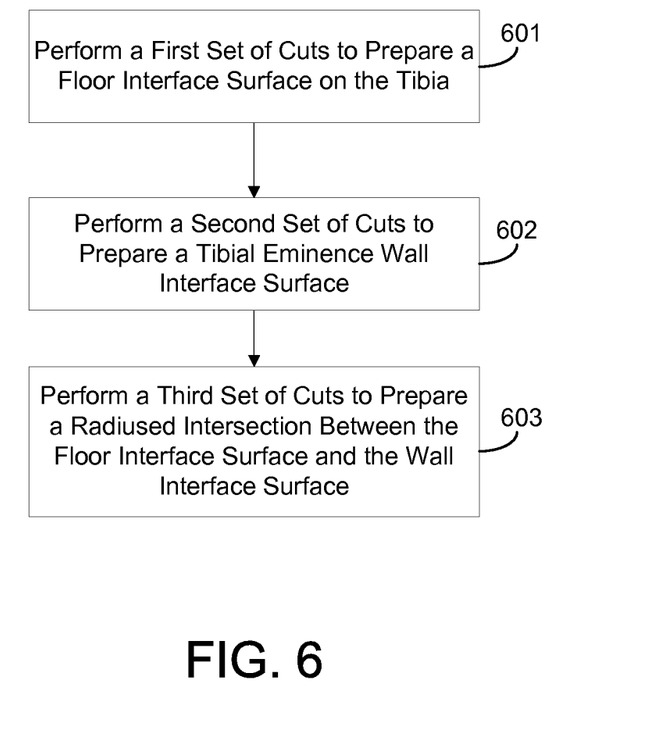
FIG. 6 illustrates a method of preparing a proximal end of a tibia to receive a prosthetic component according to an exemplary embodiment.

Preparation of the joint as described above may be performed according to an exemplary embodiment depicted in FIG. 6. A method of preparing the bone includes performing a first set of cuts to prepare a floor interface surface 151 on the tibia (step 601). The floor interface surface 151 includes a portion 151a, 151b on each side of a tibial eminence 101a, extending above the floor interface surface 151 on the tibia 101. The method further includes performing a second set of cuts to prepare a tibial eminence wall interface surface 153 (step 602). The wall interface surface 153 extends substantially perpendicular to the floor interface surface 151 between the floor interface surface 151 and a top surface 102 of the tibial eminence 101a. The method further includes performing a third set of cuts to prepare a radiused intersection between the floor interface surface and the wall interface surface (step 603). As discussed above, the sets of cuts are performed subject to a cutting restraint guide. In other embodiments, steps 601, 602, and 603 may be performed in a different order from that shown in FIG. 6. Similarly, the third set of cuts (step 603) can be performed in conjunction with step 601 or step 602 when those steps involve cutting using a rotary cutter. As mentioned above, one or more of the sets of cuts may be performed using a rotary cutter.

Figure 7:
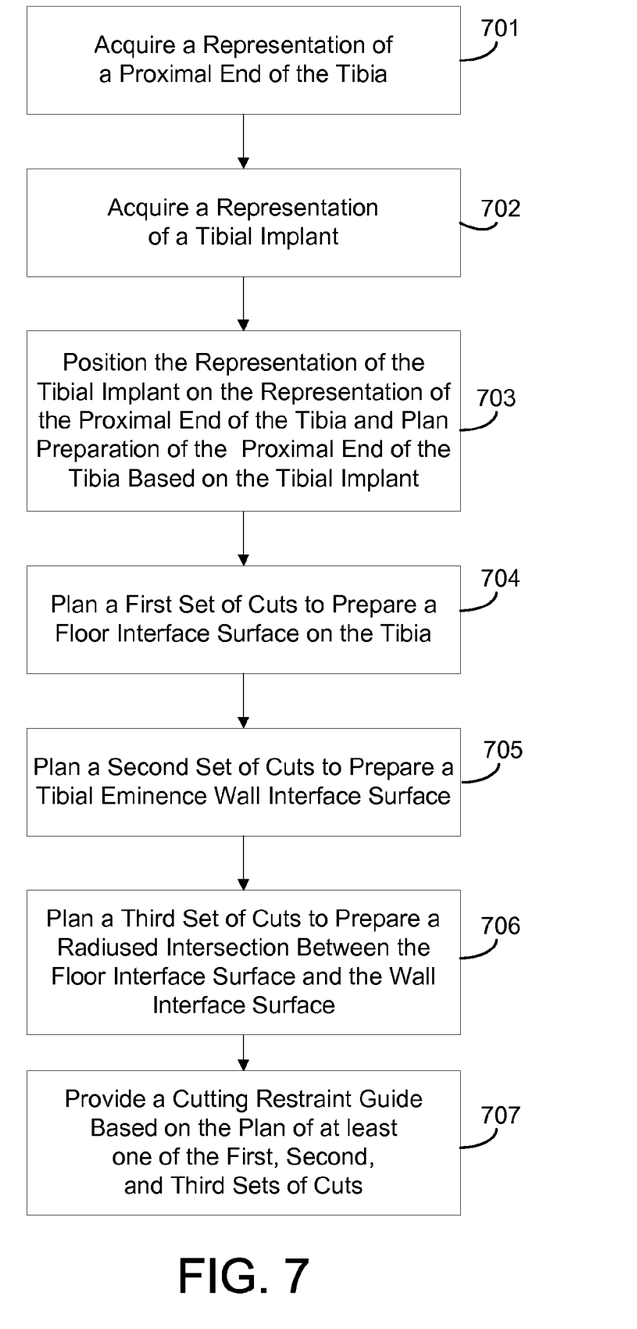
FIG. 7 illustrates a method of planning the preparation a proximal end of a tibia to receive a prosthetic component according to an exemplary embodiment.

Planning for preparation of the joint as described above may be performed according to an exemplary embodiment depicted in FIG. 7. The surgical planning method includes acquiring a representation of a proximal end of the tibia (step 701). The representation of the anatomy may be acquired by an imaging system and may include images such as CT or MRI images. The images may be acquired pre-operatively, intraoperatively, or at the time of surgical planning. The images may be loaded and acquired through surgical system 200, described below. The method also includes acquiring a representation of a tibial implant (step 702). Model implants may also be loaded and acquired through surgical system 200. The surgeon may be able to select from a number of different implant models and choose the implant that is most appropriate for the patient and the patient's anatomy. The planning method further includes positioning the representation of the tibial implant on the representation of the proximal end of the tibia and planning preparation of the proximal end of the tibia based on the tibial implant (step 703). The surgeon may be able to modify the position of the implant on the anatomy of the patient. Positioning of the model implant on the representation on the bone allows for planning the resections necessary to prepare the bone to receive the tibial implant, including planning a first set of cuts to prepare a floor interface surface 151 on the tibia 101 (step 704). The floor interface surface 151 comprises a portion 151a, 151b on each side of a tibial eminence 101a extending above the floor interface portion on the tibia. Step 705 includes planning a second set of cuts to prepare a tibial eminence wall interface surface 153. The wall interface surface 153 extends substantially perpendicular to the floor interface surface 151 between the floor interface surface 151 and a top surface 102 of the tibial eminence 101a. Step 706 includes planning a third set of cuts to prepare a radiused intersection 152 between the floor interface surface 151 and the wall interface surface 153. The method further includes providing a cutting restraint guide based on the plan of at least one of the first, second, and third sets of cuts (step 707).

An exemplary approach to ensure precise and accurate preparation of the joint according to the methods of the exemplary embodiments described above may utilize a computer-assisted surgery (CAS) system to aid the surgeon in properly aligning the tool prior to interaction with patient's anatomy and performing accurate cuts in the bone. Many CAS systems include software that allow users to electronically register certain anatomic features (e.g., bones, soft tissues, etc.), surgical instruments, and other landmarks associated with the surgical site. CAS systems may generate a graphical representation of the surgical site based on the registration of the anatomic features. The CAS software also allows users to plan certain aspects of the surgical procedure, and register these aspects for display with the graphical representation of the surgical site. For example, in a knee joint replacement procedure, a surgeon may register target navigation points, the location and depth of bone and tissue cuts, virtual boundaries that may be associated with a corresponding reference for the application of haptic force, and other aspects of the surgery.

Figure 8:
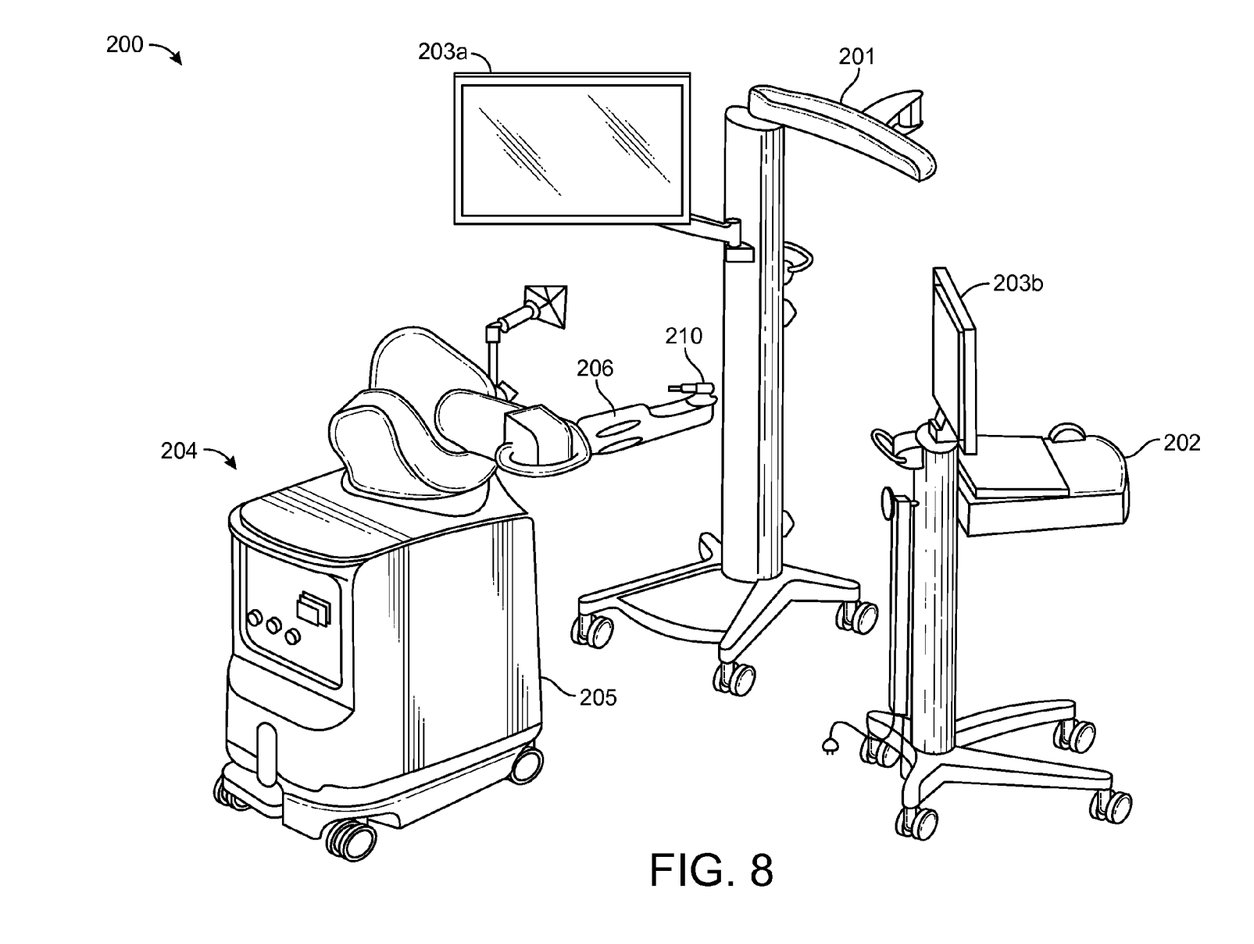
FIG. 8 illustrates a perspective view of an embodiment of a surgical system according to an exemplary embodiment.

FIG. 8 provides a schematic diagram of an exemplary computer-assisted surgery (CAS) system 200, in which processes and features associated with certain disclosed embodiments may be implemented. Surgical system 200 may be configured to perform a wide variety of orthopedic surgical procedures such as, for example, partial or total joint replacement surgeries. As illustrated in FIG. 2, surgical system 200 includes a tracking system 201, computing system 202, one or more display devices 203a, 203b, and a robotic system 204. It should be appreciated that system 200, as well as the methods and processes described herein, may be applicable to many different types of joint replacement procedures. Although certain disclosed embodiments may be described with respect to knee replacement procedures, the concepts and methods described herein may be applicable to other types of orthopedic surgeries, such as partial hip replacement, full or partial hip resurfacing, shoulder replacement or resurfacing procedures, and other types of orthopedic procedures.

Robotic system 204 can be used in an interactive manner by a surgeon to perform a surgical procedure, such as a knee replacement procedure, on a patient. As shown in FIG. 2, robotic system 204 includes a base 205, an articulated arm 206, a force system (not shown), and a controller (not shown). A surgical tool 210 (e.g., an end effector having an operating member, such as a saw, reamer, or burr) may be coupled to the articulated arm 206. The surgeon can manipulate the surgical tool 210 by grasping and manually moving the articulated arm 206 and/or the surgical tool 210.

The force system and controller are configured to provide the cutting restraint guide via control or guidance to the surgeon during manipulation of the surgical tool. The force system is configured to provide at least some force to the surgical tool via the articulated arm 206, and the controller is programmed to generate control signals for controlling the force system. In one embodiment, the force system includes actuators and a back-driveable transmission that provide haptic (or force) feedback to constrain or inhibit the surgeon from manually moving the surgical tool beyond predefined haptic boundaries defined by haptic objects as described, for example, in U.S. Pat. No. 8,010,180 and/or U.S. patent application Ser. No. 12/654,519 (U.S. Patent Application Pub. No. 2010/0170362), filed Dec. 22, 2009, each of which is hereby incorporated by reference herein in its entirety. According to one embodiment, surgical system 200 is the RIO® Robotic Arm Interactive Orthopedic System manufactured by MAKO Surgical Corp. of Fort Lauderdale, Fla. The force system and controller may be housed within the robotic system 204.

Tracking system 201 is configured to determine a pose (i.e., position and orientation) of one or more objects during a surgical procedure to detect movement of the object(s). For example, the tracking system 201 may include a detection device that obtains a pose of an object with respect to a coordinate frame of reference of the detection device. As the object moves in the coordinate frame of reference, the detection device tracks the pose of the object to detect (or enable the surgical system 200 to determine) movement of the object. As a result, the computing system 202 can capture data in response to movement of the tracked object or objects. Tracked objects may include, for example, tools/instruments, patient anatomy, implants/prosthetic devices, and components of the surgical system 200. Using pose data from the tracking system 201, the surgical system 200 is also able to register (or map or associate) coordinates in one space to those in another to achieve spatial alignment or correspondence (e.g., using a coordinate transformation process as is well known). Objects in physical space may be registered to any suitable coordinate system, such as a coordinate system being used by a process running on the surgical controller 212 and/or the computer device of the haptic device 204. For example, utilizing pose data from the tracking system 201, the surgical system 200 is able to associate the physical anatomy, such as the patient's tibia, with a representation of the anatomy (such as an image displayed on the display device 203). Based on tracked object and registration data, the surgical system 200 may determine, for example, a spatial relationship between the image of the anatomy and the relevant anatomy.

Registration may include any known registration technique, such as, for example, image-to-image registration (e.g., monomodal registration where images of the same type or modality, such as fluoroscopic images or MR images, are registered and/or multimodal registration where images of different types or modalities, such as MRI and CT, are registered); image-to-physical space registration (e.g., image-to-patient registration where a digital data set of a patient's anatomy obtained by conventional imaging techniques is registered with the patient's actual anatomy); and/or combined image-to-image and image-to-physical-space registration (e.g., registration of preoperative CT and MRI images to an intraoperative scene). The computing system 202 may also include a coordinate transform process for mapping (or transforming) coordinates in one space to those in another to achieve spatial alignment or correspondence. For example, the surgical system 200 may use the coordinate transform process to map positions of tracked objects (e.g., patient anatomy, etc.) into a coordinate system used by a process running on the computer of the haptic device and/or the surgical controller 212. As is well known, the coordinate transform process may include any suitable transformation technique, such as, for example, rigid-body transformation, non-rigid transformation, affine transformation, and the like.

The tracking system 201 may be any tracking system that enables the surgical system 200 to continually determine (or track) a pose of the relevant anatomy of the patient. For example, the tracking system 201 may include a non-mechanical tracking system, a mechanical tracking system, or any combination of non-mechanical and mechanical tracking systems suitable for use in a surgical environment. The non-mechanical tracking system may include an optical (or visual), magnetic, radio, or acoustic tracking system. Such systems typically include a detection device adapted to locate in predefined coordinate space specially recognizable trackable elements (or trackers) that are detectable by the detection device and that are either configured to be attached to the object to be tracked or are an inherent part of the object to be tracked. For example, a trackable element may include an array of markers having a unique geometric arrangement and a known geometric relationship to the tracked object when the trackable element is attached to the tracked object. The known geometric relationship may be, for example, a predefined geometric relationship between the trackable element and an endpoint and axis of the tracked object. Thus, the detection device can recognize a particular tracked object, at least in part, from the geometry of the markers (if unique), an orientation of the axis, and a location of the endpoint within a frame of reference deduced from positions of the markers.

The markers may include any known marker, such as, for example, extrinsic markers (or fiducials) and/or intrinsic features of the tracked object. Extrinsic markers are artificial objects that are attached to the patient (e.g., markers affixed to skin, markers implanted in bone, stereotactic frames, etc.) and are designed to be visible to and accurately detectable by the detection device. Intrinsic features are salient and accurately locatable portions of the tracked object that are sufficiently defined and identifiable to function as recognizable markers (e.g., landmarks, outlines of anatomical structure, shapes, colors, or any other sufficiently recognizable visual indicator). The markers may be located using any suitable detection method, such as, for example, optical, electromagnetic, radio, or acoustic methods as are well known. For example, an optical tracking system having a stationary stereo camera pair sensitive to infrared radiation may be used to track markers that emit infrared radiation either actively (such as a light emitting diode or LED) or passively (such as a spherical marker with a surface that reflects infrared radiation). Similarly, a magnetic tracking system may include a stationary field generator that emits a spatially varying magnetic field sensed by small coils integrated into the tracked object.

Computing system 202 may be communicatively coupled to tracking system 201 and may be configured to receive tracking data from tracking system 201. Based on the received tracking data, computing system 202 may determine the position and orientation associated with one or more registered features of the surgical environment, such as surgical tool 210 or portions of the patient's anatomy. Computing system 202 may also include surgical planning and surgical assistance software that may be used by a surgeon or surgical support staff during the surgical procedure. For example, during a joint replacement procedure, computing system 202 may display images related to the surgical procedure on one or both of the display devices 203a, 203b.

Figure 9:
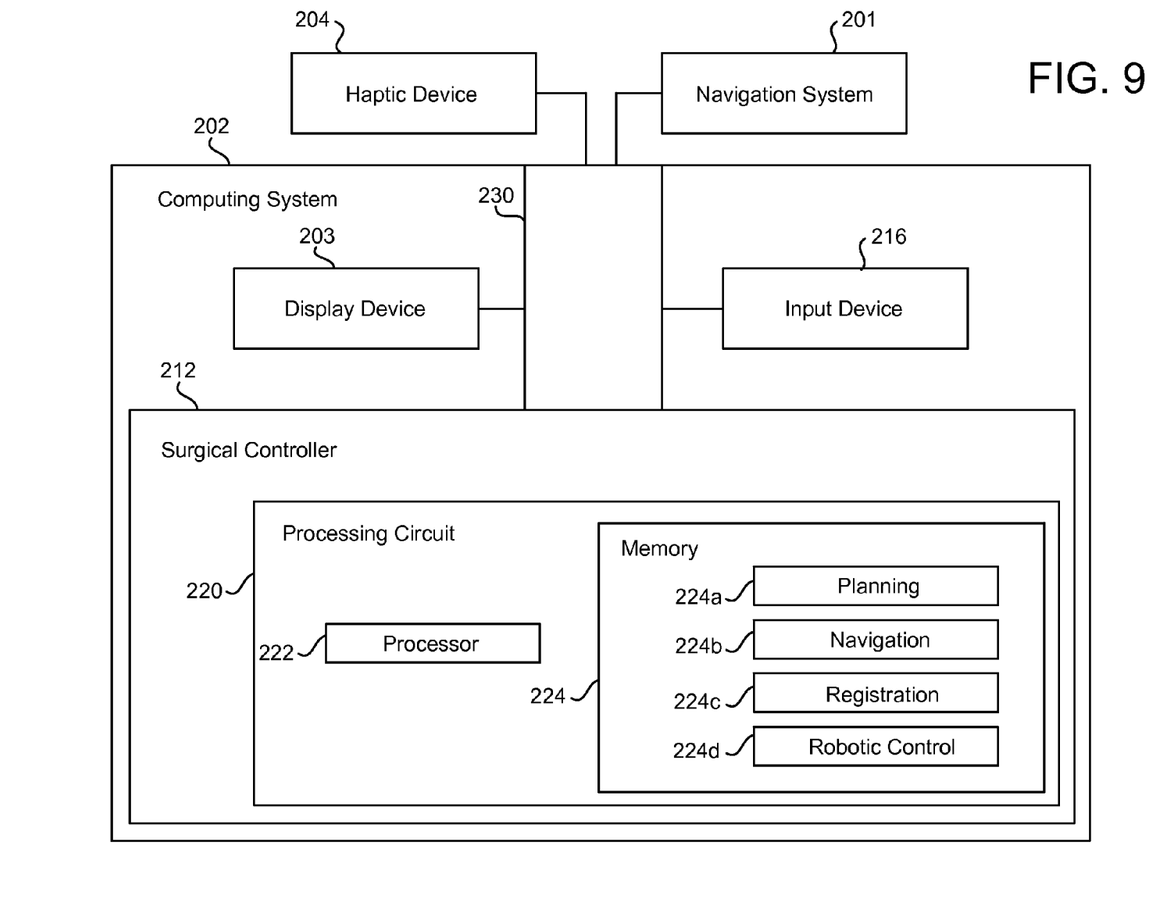
FIG. 9 illustrates a block diagram of a surgical system according to an exemplary embodiment.

Computing system 202 (and/or one or more constituent components of surgical system 200) may include hardware and software for operation and control of the surgical system 200. Such hardware and/or software is configured to enable the system 200 to perform the techniques described herein. Referring to FIG. 9, the computing system 202 includes a surgical controller 212, a display device 203, and an input device 216.

The surgical controller 212 may be any known computing system but is preferably a programmable, processor-based system. For example, the surgical controller 212 may include a microprocessor, a hard drive, random access memory (RAM), read only memory (ROM), input/output (I/O) circuitry, and any other known computer component. The surgical controller 212 is preferably adapted for use with various types of storage devices (persistent and removable), such as, for example, a portable drive, magnetic storage, solid state storage (e.g., a flash memory card), optical storage, and/or network/Internet storage. The surgical controller 212 may comprise one or more computers, including, for example, a personal computer or a workstation operating under a suitable operating system and preferably includes a graphical user interface (GUI).

Referring again to FIG. 9, in an exemplary embodiment, the surgical controller 212 includes a processing circuit 220 having a processor 222 and memory 224. Processor 222 can be implemented as a general purpose processor executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit), a group of processing components, or other suitable electronic processing components. Generally, a processor will receive instructions and data from a read only memory or a random access memory or both. Memory 224 (e.g., memory, memory unit, storage device, etc.) comprises one or more devices (e.g., RAM, ROM, Flash-memory, hard disk storage, etc.) for storing data and/or computer code for completing or facilitating the various processes described in the present application. Memory 224 may be or include volatile memory or non-volatile memory. Memory 224 may include database components, object code components, script components, or any other type of information structure for supporting the various activities described in the present application. According to an exemplary embodiment, memory 224 is communicably connected to processor 222 and includes computer code for executing one or more processes described herein. The memory 224 may contain a variety of modules, each capable of storing data and/or computer code related to specific types of functions. In one embodiment, memory 224 contains several modules related to surgical procedures, such as a planning module 224*a*, a navigation module 224*b*, a registration module 224*c*, and a robotic control module 224*d*.

Alternatively or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate components or media (e.g., multiple CDs, disks, or other storage devices). Accordingly, the computer storage medium may be tangible and non-transitory.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an embodiment of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

Referring to the embodiment of surgical system 200 depicted in FIG. 9, the surgical controller 212 further includes a communication interface 230. The communication interface 230 of the computing system 202 is coupled to a computing device (not shown) of the robotic system 204 via an interface and to the tracking system 201 via an interface. The interfaces can include a physical interface and a software interface. The physical interface of the communication interface 230 can be or include wired or wireless interfaces (e.g., jacks, antennas, transmitters, receivers, transceivers, wire terminals, etc.) for conducting data communications with external sources via a direct connection or a network connection (e.g., an Internet connection, a LAN, WAN, or WLAN connection, etc.). The software interface may be resident on the surgical controller 212, the computing device (not shown) of the robotic system 204, and/or the tracking system 201. In some embodiments, the surgical controller 212 and the computing device (not shown) are the same computing device. The software may also operate on a remote server, housed in the same building as the surgical system 200, or at an external server site.

Computing system 202 also includes display device 203. The display device 203 is a visual interface between the computing system 52 and the user. The display device 203 is connected to the surgical controller 212 and may be any device suitable for displaying text, images, graphics, and/or other visual output. For example, the display device 203 may include a standard display screen (e.g., LCD, CRT, OLED, TFT, plasma, etc.), a touch screen, a wearable display (e.g., eyewear such as glasses or goggles), a projection display, a head-mounted display, a holographic display, and/or any other visual output device. The display device 203 may be disposed on or near the surgical controller 212 (e.g., on the cart as shown in FIG. 8) or may be remote from the surgical controller 212 (e.g., mounted on a stand with the tracking system 56). The display device 203 is preferably adjustable so that the user can position/reposition the display device 203 as needed during a surgical procedure. For example, the display device 203 may be disposed on an adjustable arm (not shown) or to any other location well-suited for ease of viewing by the user. As shown in FIG. 8 there may be more than one display device 203 in the surgical system 200.

The display device 203 may be used to display any information useful for a medical procedure, such as, for example, images of anatomy generated from an image data set obtained using conventional imaging techniques, graphical models (e.g., CAD models of implants, instruments, anatomy, etc.), graphical representations of a tracked object (e.g., anatomy, tools, implants, etc.), constraint data (e.g., axes, articular surfaces, etc.), representations of implant components, digital or video images, registration information, calibration information, patient data, user data, measurement data, software menus, selection buttons, status information, and the like.

In addition to the display device 203, the computing system 202 may include an acoustic device (not shown) for providing audible feedback to the user. The acoustic device is connected to the surgical controller 212 and may be any known device for producing sound. For example, the acoustic device may comprise speakers and a sound card, a motherboard with integrated audio support, and/or an external sound controller. In operation, the acoustic device may be adapted to convey information to the user. For example, the surgical controller 212 may be programmed to signal the acoustic device to produce a sound, such as a voice synthesized verbal indication "DONE," to indicate that a step of a surgical procedure is complete. Similarly, the acoustic device may be used to alert the user to a sensitive condition, such as producing a tone to indicate that a surgical cutting tool is nearing a critical portion of soft tissue or is approaching the haptic boundary.

To provide for other interaction with a user, embodiments of the subject matter described in this specification can be implemented on a computer having input device 216 that enables the user to communicate with the surgical system 200. The input device 216 is connected to the surgical controller 212 and may include any device enabling a user to provide input to a computer. For example, the input device 216 can be a known input device, such as a keyboard, a mouse, a trackball, a touch screen, a touch pad, voice recognition hardware, dials, switches, buttons, a trackable probe, a foot pedal, a remote control device, a scanner, a camera, a microphone, and/or a joystick. For example, input device 216 can allow the user manipulate the haptic boundary as discussed above. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

General surgical planning and navigation to carry out the exemplary methods described above, and including haptic control and feedback as described in connection with surgical system 200, may be performed by a computerized surgical system such as that described in U.S. Pat. No. 8,010,180 "Haptic Guidance System and Method" to Quaid et al., which is incorporated herein by reference in its entirety.

The construction and arrangement of the systems and methods as shown in the various exemplary embodiments are illustrative only. Although only a few embodiments have been described in detail in this disclosure, many modifications are possible. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

What is claimed is:

1. A surgical planning method for preparing a tibia to receive a tibial implant component, comprising:
    acquiring a virtual representation of a proximal end of the tibia;
    acquiring a virtual representation of a tibial implant;
    positioning the virtual representation of the tibial implant on the virtual representation of the proximal end of the tibia;
    planning preparation of the proximal end of the tibia based on the tibial implant, comprising:
        planning a first set of cuts to prepare a floor interface surface on the tibia, wherein the floor interface surface comprises a portion on each side of a tibial eminence extending above the floor interface portion on the tibia;
        planning a second set of cuts to prepare a tibial eminence wall interface surface, wherein the wall interface surface extends substantially perpendicular to the floor interface between the floor interface surface and a top surface of the tibial eminence; and
        planning a third set of cuts to prepare a radiused intersection between the floor interface surface and the wall interface surface;
    generating a virtual object specific to the plan of at least one of the first, second, and third sets of cuts and associating the virtual object with the virtual representation of the proximal end of the tibia, wherein the virtual object defines a cutting boundary configured to constrain movement of a surgical tool while the surgical tool is used for performing at least one of the first, second, and third sets of cuts.

2. The method of claim 1, further comprising providing a mechanical cutting guide configured for implementing at least one of the planned sets of cuts.

3. The method of claim 1, wherein generating a virtual object comprises generating a haptic boundary configured to be applied to a surgical tool to constrain the tool against penetration of the haptic boundary.

4. The method of claim 1, wherein planning the third set of cuts comprises planning the third set of cuts to prepare a radiused intersection between the floor interface surface and the wall interface surface using a rotary surgical cutting tool.

5. The method of claim 4, wherein planning the first set of cuts or planning the second set of cuts comprises, respectively, planning the first set of cuts to prepare a floor interface surface on the tibia using the rotary surgical cutting tool or planning the second set of cuts to prepare a tibial eminence wall interface surface using the rotary surgical cutting tool.

6. The method of claim 1, further comprising providing a surgical system configured to carry out the surgical plan, the surgical system comprising:
    a surgical device configured to hold a surgical tool and be manipulated by a user to perform preparation of the tibia;
    a feedback mechanism providing the cutting restraint guide and configured to supply feedback to the user manipulating surgical device based on a relationship between the bone and the surgical device; and
    a computing system programmed to control the feedback mechanism to provide guidance to the user while the user manipulates the surgical device.

7. The method of claim 6, wherein the computing system is further configured to generate a haptic boundary, and wherein the feedback mechanism provides a haptic force applied to the surgical tool to constrain the tool against penetration of the haptic boundary.

* * * * *